(12) United States Patent
Zanarotti et al.

(10) Patent No.: US 9,149,493 B2
(45) Date of Patent: Oct. 6, 2015

(54) COMPOSITIONS FOR BOWEL CLEANSING AND USE THEREOF

(75) Inventors: Alessandro Zanarotti, Milan (IT); Gabriele Brunetti, Milan (IT); Sergio Cecchetti, Pozzuolo Martesana (IT)

(73) Assignee: ALFA WASSERMANN SPA, Alanno Scalo (IT)

( * ) Notice: Subject to any disclaimer, the term of this patent is extended or adjusted under 35 U.S.C. 154(b) by 272 days.

(21) Appl. No.: 13/304,976

(22) Filed: Nov. 28, 2011

(65) Prior Publication Data
US 2013/0136806 A1 May 30, 2013

(51) Int. Cl.
| | | |
|---|---|---|
| *A61K 33/00* | (2006.01) |
| *A61K 31/765* | (2006.01) |
| *A61K 45/06* | (2006.01) |
| *A61K 31/80* | (2006.01) |
| *A61K 33/14* | (2006.01) |
| *A61K 33/04* | (2006.01) |
| *A61K 31/195* | (2006.01) |

(52) U.S. Cl.
CPC .............. *A61K 33/00* (2013.01); *A61K 31/195* (2013.01); *A61K 31/765* (2013.01); *A61K 31/80* (2013.01); *A61K 33/04* (2013.01); *A61K 33/14* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 7,332,184 B2 * | 2/2008 | Vanner et al. ................. | 424/606 |
| 2005/0003021 A1 | 1/2005 | Suglyama et al. | |
| 2008/0260682 A1 * | 10/2008 | Rose et al. ................ | 424/78.38 |
| 2013/0136806 A1 | 5/2013 | Zanarotti | |

FOREIGN PATENT DOCUMENTS

| | | |
|---|---|---|
| DE | 202010010312 U1 | 12/2010 |
| EP | 0955065 | 11/1999 |
| WO | 2009052256 | 4/2009 |

OTHER PUBLICATIONS

Wikipedia entry for Crystal Light [downloaded on Mar. 28, 2013 from the website http://en.wikipedia.org/wiki/Crystal_Light].*
Sudduth et al., Gastrointestinal Endosc 42: 413 (1995).*
Lazzaroni et al., Aliment Pharmacol Ther 7: 655 (1993).*
DE202010010312 in machine translation.*
DE202010010312 in machine translation; 2015.*
Burke et al., Postgrad Med J 64: 772-774 (1988).*
E-Z-M: "LO SO Prep", Mar. 30, 2008, Retrieved from the Internet: URL:http://www.ezem.com/pdf/1303811_loso.p df> [retrieved on Dec. 7, 2009].
TorrinoMedica: "SELG" Feb. 28, 1197, Retrieved from the Internet: URL:http://www.torrinomedica.it/studio/generaframe.asp?variabile=http://www.torrinomeidca.it/farmaci/schedetechniche/SELG.asp> [retrieved on Dec. 7, 2009].
Wexner SD et al: "A concensus document on bowel preparation prior to colonoscopy" Apr. 30, 2006, Retrieved from the Internet: URL:http://www.sages.org/publication/id/ BO WEL/> [retrieved on Dec. 7, 2009].
European search report, for EP Application No. 09174788.1-2123, dated Dec. 17, 2009.
EU Clinial Trials Register for Trial No. 2010-019317-22 by Promefarm.
English language version of German Application No. DE202010010312 U1 and Application Request dated Jul. 16, 2010.
German Field Codes downloaded from the German Patent Office Web Site, http://www.dpma.de/docs/service/e_dienstleistungen/dpmaregister/register_recherchefelder_patgbm_en.pdf (pages manually numbered), Aug. 19, 2013.
Guidelines for Examination in the European Patent Office Rules, Aug. 19, 2013.
Rowe et al., eds., "Colloidal Silicon Dioxide," Handbook of Pharmaceutical Excipients, 5th Edition. London: Pharmaceutical Press, pp. 188-191 (2006).
Sweetman, Sean C., ed. Martindale: The Complete Drug Reference, 34th Edition, London, Pharmaceutical Press (2005).
Google Search Result for the search query ["PMF 104BC1/10" Easygol] for date range Jan. 1, 2001-Nov. 27, 2010.
EU Clinical Trial Register for Trial No. 2010-019317-22 by Promefarm.
English Language Version of German Application No. DE202010010312U1 and Application Request dated Jul. 16, 2010.
German Field Codes downloaded from the German Patent Office Web Site, http://www.dpma.de/docs/service/e_dienstleistungen/dpmaregister/register_recherchefelder_patgbm_en.pdf (pages manually numbered).
Guidelines for Examination in the European Patent Office Rules.
Rowe et al., eds, "Colloidal Silicon Dioxide," Handbook of Pharmaceutical Excipients, 5th Edition. London: Pharmaceutical Press, pp. 188-191 (2006).
Shaver et al., "Improvement of Oral Colonic Lavage with Supplemental Simethicone," Digestive Disease and Sciences 33(2):185-188 (1998).

* cited by examiner

*Primary Examiner* — Sue Liu
*Assistant Examiner* — Thor Nielsen
(74) *Attorney, Agent, or Firm* — Silvia Salvadori P.C.

(57) ABSTRACT

The present invention relates to a dry composition for reconstitution in water comprising polyethylene glycol (PEG), optionally sodium sulphate, citric acid, sodium citrate, sodium chloride, potassium chloride, simethicone, effective for bowel cleansing, in particular of colon, prior to diagnostic, surgical or therapeutical procedures, in particular colonoscopy.

3 Claims, No Drawings

COMPOSITIONS FOR BOWEL CLEANSING AND USE THEREOF

TECHNICAL FIELD OF THE INVENTION

The present invention relates to a composition useful for bowel cleansing prior to carry out diagnostic, surgical or therapeutic procedures in the bowel, in particular in the colon (such as for example colonoscopy, radiology and colon surgery).

BACKGROUND OF THE INVENTION

The preparation of bowel, in particular of colon, prior to diagnostic, surgical or therapeutical procedures, for example colonoscopy, is a crucial prerequisite for a successful procedure.

In the past, the bowel preparation was carried out with high volume solutions (7-12 liters) with or without non-absorbable sugars (such as mannitol) which had respectively the inconvenience of causing water retention and promoting the production of potentially dangerous high quantity of gas.

In other cases, hyperosmotic saline laxatives were used, which had a drastic cathartic effect on bowel with the risk, for example, of dehydration, electrolyte imbalances, cardiovascular and renal complications, etc. . . . .

Subsequently, a polyethylene glycol (PEG) based solution was first described by the Fordtran's group in '80 (WO87/00754 and Davis G R, Santa Ana C A, Morawski S G, Fordtran J S. Development of a lavage solution associated with minimal water and electrolyte absorption or secretion. Gastroenterology 1980; 78: 991-5).

This formulation has the advantage of being poorly absorbed during gut transit and thus avoiding retention or loss of fluids and electrolytes from the body.

In general, PEGs are compounds of low toxicity and are largely used in pharmaceutical preparations as excipient.

The solution proposed by Fordtran, together with its variants, are a well established preparation for cleansing the colon before diagnostic procedures and they are still the most common preparation used for this purpose.

In order to obtain an adequate bowel preparation, about four liters of this formulation in combination with a diet rich in fluids and poor in fibres are still needed for at least 3 days prior to the procedure.

Furthermore, those formulations are frequently characterized by a poor palatability.

Also a variant of Fordtran's preparation with in addition simethicone has been proposed (Shaver W A, Storms P, Peterson W L. Improvement of oral colonic lavage with supplemental simethicone. Dig Dis Sci 1988; 33(2):185-8).

Nevertheless, the quality of the colon preparation is still reported as poor or unacceptable in about 15-20% of the colonoscopies. This is probably due to the fact that 10 to 15% of patients do not complete the preparation because of poor palatability and/or large volume of the administered solution.

Inadequate cleansing of the colon may lead to: a) increased risk of false negative (missed diagnosis), b) more frequent complications, c) longer procedures with increased discomfort for the patient, d) incompleteness of the procedure with the need to repeat the investigation.

There is therefore the need to found new solutions for bowel cleansing with an improved palatability and/or with a reduced total volume to ingest.

EP 1 567 193-B1 describes a composition comprising, per liter of aqueous solution, from 30 to 350 g polyethylene glycol, from 3 to 20 g of an ascorbic acid component selected from the group consisting of ascorbic acid, a salt of ascorbic acid, or a mixture thereof, an alkali metal or alkaline earth metal sulphate, preferably from 1 to 15 g thereof, and optionally one or more electrolytes selected from sodium chloride, potassium chloride, and sodium hydrogen carbonate, and preferably also comprising flavourings, effective in cleansing the gut in preparation for a endoscopy, especially colonoscopy. Such composition allows the colon cleansing with a reduced volume.

The present invention represents a further step toward patient acceptance and compliance.

SUMMARY OF THE INVENTION

The present invention relates to a dry composition for reconstitution in water comprising:
(a) polyethylene glycol (PEG),
(b) optionally sodium sulphate,
(c) citric acid,
(d) sodium citrate,
(e) sodium chloride,
(f) potassium chloride,
(g) simethicone.

The invention also concerns the use of a dry composition for reconstitution in water comprising polyethylene glycol (PEG), optionally sodium sulphate, citric acid, sodium citrate, sodium chloride, potassium chloride, simethicone, for the manufacture of a preparation for bowel cleansing.

When the dry composition for reconstitution in water does not comprise sodium sulphate, a laxative is needed to obtain the desired cathartic effect.

Furthermore, it regards an aqueous solution obtainable by reconstitution in water of a dry composition according to the invention.

DETAILED DESCRIPTION OF THE INVENTION

The present invention relates to a dry composition for reconstitution in water comprising:
(a) polyethylene glycol (PEG),
(b) optionally sodium sulphate,
(c) citric acid,
(d) sodium citrate,
(e) sodium chloride,
(f) potassium chloride,
(g) simethicone.

Administration of the reconstituted lavage solution induces watery stools useful for bowel cleansing prior to diagnostic, surgical or therapeutical procedures, in particular to be carried out in the colon, such as for example radiology, colon surgery and in particular colonoscopy.

Citric acid and sodium citrate were included in the formulation for the purpose of improving the taste and thus increasing patient acceptance and compliance. A clinical study was carried out to test the new formulations.

In particular, a clinical study (phase I-II) was performed to investigate the pharmacodynamics and pharmacokinetics of citric acid and sodium citrate in healthy volunteers following administration of a lavage solution according to formulation 1 of present invention. It was found that citric acid and sodium citrate contained in formulation 1 are poorly absorbed as there was no significant increase of urinary excretion of citric acid or citrates. This result is in contrast with the current knowledge on the properties and use of citrates: when administered alone, they are in fact almost entirely absorbed in the small intestine, and are eliminated unchanged in the urine.

When 2 liters of formulation 1 were compared to 4 liters of reference preparation (SELG® 1000), the cathartic effect was found to be equal.

When 2 liters of formulation 1 were compared to 2 liters of reference preparation (SELG® 1000), the cathartic effect of formula was found to be greater than reference preparation.

Thus the study shows an unexpected marked cathartic effect due to the presence of citric acid and sodium citrate (citrates) in the formulation used. In other words, citrates administered as components of the formulation used for the study, are not absorbed and cause a significant increase of the cathartic effect thus allowing the administration of a low volume solution.

It has been surprisingly found that it is possible to achieve a bowel cleansing satisfactory for carrying out a diagnostic, surgical or therapeutical procedure in the bowel, in particular in the colon, administering a low volume lavage solution comprising polyethylene glycol (PEG), optionally sodium sulphate, citric acid, sodium citrate, sodium chloride, potassium chloride, simethicone.

When the dry composition for reconstitution in water does not comprise sodium sulphate, a laxative is administered few hours, about 3-4 hours, before the administration of the lavage solution.

Therefore, the lavage solution according to the invention is able to induce an equivalent laxative effect at a lower dose with respect to the conventional cleansing solution.

For obtaining a satisfactory bowel, in particular colon, cleansing effect, i.e. the removal of solid residuals and the cleansing of intestinal walls, it is sufficient to administrate the solution according to the invention in a quantity of about 2 liter, whereas 4 liters are to be administered for obtaining a comparable effect when using conventional cleansing solutions.

The presence of citric acid and sodium citrate increases the overall cathartic effect, e.g. increases water stool volume, reducing the total volume of the lavage solution to be taken.

Furthermore, citric acid and sodium citrate improve palatability as well as ease the ingestion of the lavage solution, so that the lavage solution according to the present invention is easier to take and more accepted by patients. Thus, advantageously improving the compliance rate of patients achieving a good and acceptable preparation for the subsequent procedure.

The association with a stimulant laxative, such as for example bisacodyl, reduces the amount of liquid to swallow, i.e. one of the major problems identified by treated patients.

Polyethylene glycol (PEG), also known as Macrogol, has an average molecular weight preferably varying from 3350 to 4000, more preferably the average molecular weight is of 4000.

Preferably, PEG is comprised in a range from 105 g to 121.5 g per liter of aqueous solution.

PEG undergoes virtually no absorption from the gastrointestinal tract and passes unchanged through the intestine. Only very minimal amounts (<0.1%) may be absorbed and are excreted in the urine.

PEG exerts the main osmotic activity, indeed the high molecular weight exerts an osmotic effect retaining water and electrolytes in the intestine.

The unabsorbed fluid accounts for the laxative property by increasing the weight of the fecal effluent.

Also sodium sulphate, citric acid and sodium citrate have osmotic activity.

Sodium sulphate anhydrous is preferably used in a range varying from 0 g to 7.5 g per liter, more preferably 7.5 g per liter.

Sodium sulphate is used and useful also for its laxative properties.

Citric acid is a nontoxic substance which is found naturally in the body and is a common ingredient of a normal diet.

The composition may contain anhydrous citric acid from 1.626 to 2.500 g per liter.

Anhydrous sodium citrate may be in the composition in a quantity ranging from 2.132 g to 3.726 g per liter.

The content of sodium chloride is usually from 1.27 g to 1.46 g per liter.

Potassium chloride is normally within a range of from 0.382 g to 0.740 g per liter.

Sodium chloride and potassium chloride are important to prevent absorption or loss of electrolytes and water, maintaining the osmolarity within physiologically acceptable ranges.

As regards simethicone, its therapeutic indications are dyspepsia, relief of flatulence and abdominal discomfort due to excess of gastrointestinal gas and gastroesophageal reflux disease. It is also used as antifoaming agent in radiology or endoscopy of the gastrointestinal tract.

Simethicone is a well established antifoam agent and improves the visualisation of the mucosa.

The laxative may be a stimulant laxative, such as for example bisacodyl, senna, sodium picosulphate.

The laxative may be administered in association with the lavage solution, in such cases the dry composition does not comprise sodium sulphate.

In particular, 10-20 mg of bisacodyl may be administered prior to the intake of about 2 liters of the lavage solution.

The dry composition may normally further comprises proper excipients, such as for example conventional sweeteners, such as acesulfame potassium, etc., and flavours, such as orange, lime, etc., in order to obtain a final product with an acceptable taste.

The dry composition may be in powder, granular or any other suitable form. Powder is the preferred form.

In a preferred embodiment the dry composition may be furnished in unit dosage form, such as for example in a sachet or in a bottle.

The lavage solution of the present invention is mildly hyperosmotic and may have an osmolarity preferably about 400-500 mOsmol/l when the lavage solution comprises sodium sulphate otherwise the osmolarity is about 290 mOsmol/l.

The pH of the lavage solution may be comprised between 3.9 and 5.0, preferably from about 4.3 to 4.8.

In a preferred embodiment, a dry composition reconstituted in water comprising:
(a) polyethylene glycol (PEG),
(b) citric acid,
(c) sodium citrate,
(d) sodium chloride,
(e) potassium chloride,
(f) simethicone,
and a stimulant laxative such as bisacodyl, senna, sodium picosulphate, may be a combined preparation for separate or sequential use in bowel cleansing.

Anyway, when a hyperosmotic solution is administered, it is recommended that additional clear liquid (e.g. water, fruit juice, soft drink, tea, etc.) is taken during the bowel preparation in order to avoid loss of fluid and electrolytes from the body.

It is further provided a possible method for administering the solution containing sodium sulphate (formulation 1) that comprises the following steps:

If the diagnostic investigation or procedure (for example colonoscopy) is planned early in the morning:
(a) the day before the exam, at about 15.00 pm, drink 1 L of solution over 1-2 hours (250 ml over 15-20 min.);
(b) take at least 500 ml of additional clear liquid (water, fruit juice, soft drink, tea/coffee without milk);
(c) take a rest of about 1-2 hours;

(d) at about 19.00 pm drink the second liter of solution over 1-2 hours (250 ml over 15-20 min.);

(e) take at least 500 ml of additional clear liquid.

If the diagnostic investigation or procedure (for example colonoscopy) is planned late in the morning or in the afternoon:

(a) the day before the exam, at about 19.00 pm, drink 1 L of solution over 1-2 hours (250 ml over 15-20 min.);

(b) take at least 500 ml of additional clear liquid (water, fruit juice, soft drink, tea/coffee without milk);

(c) on the morning of colonoscopy: at about 7.00 or 8.00 am, take 1 L of solution over 1-2 hours (250 ml over 15-20 min.);

(d) take at least 500 ml of additional clear liquid (water, soft drink).

It is recommended to leave at least two hours between the end of preparation and the time of colonoscopy.

The following non-limitative examples further describe the invention.

EXAMPLES

1 Formulation Examples

The lavage solution is prepared mixing with water the relevant dry composition up to 500 ml of lavage solution, shaking energetically several times to ensure that the ingredients are dissolved and the obtained solution is homogeneous.

The solution is more palatable if chilled before administration. The reconstituted solution should be refrigerated and used within 24-48 hours.

1.1 Formulation 1

A dry composition comprising:
52.500 g of PEG 4000,
3.750 g of sodium sulphate anhydrous,
1.863 g of sodium citrate tribasic dihydrate,
0.813 g of citric acid anhydrous,
0.730 g of sodium chloride,
0.370 g of potassium chloride,
0.080 g of simethicone,
0.080 g of lime flavour,
0.130 g of acesulfame potassium.
is reconstituted with water up to 500 ml.

The osmolarity of the lavage solution is about 440 mOsmol/l.

2 liters of the lavage solution are administered together with 1 liter of water or.

1.2 Formulation 2

A dry composition comprising:
60.742 g of PEG 4000,
1.066 g of sodium citrate,
1.250 g of citric acid anhydrous,
0.635 g of sodium chloride,
0.191 g of potassium chloride,
0.080 g of simethicone,
0.080 g of silicon dioxide,
0.326 g of orange flavour,
0.129 g of acesulfame potassium.
is reconstituted with water up to 500 ml.

The osmolarity of the lavage solution is about 290 mOsmol/l.

2 liters of the lavage solution are administered after the administration of a stimulant laxative, bisacodyl.

2. Pharmacodynamics

The main active ingredient of the formulation 1 (F1) as well as SELG® 1000, the reference formulation largely clinically employed in Europe, is PEG 4000. The amount of PEG is 105 g vs 58.3 g and of sodium sulphate 7.5 g vs 5.69 g to be dissolved in 1 L of water is higher for F1 than for SELG®; however the total amount of PEG (210 g vs 233.2) and sodium sulphate (15 g vs 22.8 g) to be taken by the patient for the bowel preparation is lower with F1 than with SELG® 1000.

The effect of the formulation 1 at different doses on stool output was determined in phase II study carried out in healthy volunteers.

F1 at the 3 ascending doses T1, T2 and T3 showed a dose-response relationship in terms of total stool weight.

In the efficacy evaluation the highest dose of F1 2 L, was not inferior to the reference product SELG® 1000 in terms of cathartic effect.

The large amount of non-absorbable fluid results in watery diarrhea, which should efficiently remove any solid residuals from the intestine.

Phase 3 Clinical Trials

3. Clinical Data

A comprehensive clinical development plan has been implemented on both formulations 1 and 2

3.1 Formulation 1 (PMF-104)

A total of 856 patients have been enrolled in clinical studies to evaluate the efficacy, safety, patient compliance and acceptability of the product for bowel preparation before colonoscopy.

In a first randomized controlled trial carried on 422 patients undergoing colonoscopy, a successful colon cleansing was observed in 73.6% of patients on PMF 104 as compared with 72.3% on the reference PEG 4 L.

Mucosal visibility was better (62.9% graded as optimal) in patients with PMF-104 than in patients (54.1% graded as optimal) on PEG 4 L.

Patient compliance was significantly better ($p<0.05$) for PMF-104 vs reference drug as well as patient acceptability ($p<0.01$).

A second phase-III, randomised controlled, multicentre trial of PMF-104 vs PEG-Ascorbate (Moviprep) has been carried out on 408 patients.

Colon cleansing was successful in 78.3% of patients in the PMF-104 group compared to 74.3% in the PEG-ASC-group. The examination was completed (cecum reached) in 94.8% of the PMF-104 group and in 96.4% of the PEG-ASC group. Mucosal visibility was optimal to adequate in 92.9% of the PMF-104 group compared to 93.5% in the PEG-ASC-group. Overall, 42 adverse events occurred but only 17 were considered medication related; 48% were seen in the PMF-104 group and 52% in the PEG-ASC group. The most frequent AE was headache. No serious adverse event or death occurred during the study. No patient discontinued the study because of an AE. Most patients in both groups reported no GI-symptoms (62.9% in the PMF-104 group vs. 59.6% in PEG-ASC group) following intake of the study medication. The acceptance of the medication was good, the willingness to repeat the same bowel preparation was estimated as 90.2% for PMF-104 group compared to 90.7% in the PEG-ASC-group.

This study demonstrated that the new bowel formulation PMF-104 is equally effective for bowel preparation before colonoscopy as compared to the marketed medicinal product PEG-ASC. It is as safe and well tolerated, patient acceptance and compliance are comparable to the reference medication.

3.2 Formulation 2 (PMF-105)

A total of 825 patients have been enrolled in 3 clinical studies to evaluate the efficacy, safety, patient compliance and acceptability of PMF-105 for bowel preparation before colonoscopy.

In a first Phase-III clinical trial the efficacy of 2 new protocols of preparation with PMF-105, vs conventional bowel prep has been evaluated in 153 patients.

The new mixed low-volume preparation regimen (PMF-105+bisacodyl) administered on the day before or the same day of colonoscopy was as effective as the split reference PEG regimen. Higher tolerability and better patient compliance and acceptability (90-92% vs 49%) were obtained.

PMF-105 in combination with bisacodyl has been also compared with PEG-ASC (Moviprep) in a second multicentre study on 408 patients.

In the planned PP population (n=376), successful bowel prep was 79.1% in PMF-105+bisacodyl and 70.4% in Prep PEG-ASC (p<0.05). Mucosal visibility was evaluated as optimum in 56.1% of PMF-105+bisacodyl vs 46.6% in the PEG-ASC (p<0.05). There were no serious adverse events (AE) in either treatment group. Two subjects in the PEG-ASC group discontinued the study because of AE (both for vomiting). Frequency (and severity) of nausea (30% vs 28.9%), bloating (23.5% vs 21.8%), abdominal pain/cramps (17% vs 15.2%) did not differ between the two preparations.

The new PMF-105 in combination with bisacodyl was more effective than PEG-ASC for outpatient colonoscopy. Tolerability, safety, acceptability and compliance of the two low volume bowel preparations were similar.

In a third randomised controlled trial on 264 patients PMF-105 was compared to the standard 4 L PEG solution (Isocolan) was carried out. In this study a new protocol administration of PMF-105 was used according the American College of Gastroenterology recommended i.e. the use of split dose administration for improving the quality of bowel preparation. In this study PMF-105 1 L was taken the eve of examination and the remaining 1 L at 07.00 of the same day of colonoscopy.

A successful bowel cleansing was reported in 92.8% of patients receiving PMF-105+bisacodyl and 92.1% of patients receiving PEG-4L, with no statistically significant difference for any of the bowel segments.

Acceptability rate significantly favoured PMF-105/bisacodyl vs PEG-4L (90.6% vs 77%; p=<0.001).

Data about patients compliance (100% percentage of drunk solution) provided a statistically significant difference showing the superiority of PMF-105 (PMF-105+bisacodyl 97.1% vs PEG 4 L 87.3%).

The new PMF-105 formulation administered as a split regimen in combination with bisacodyl provided an equivalent bowel cleansing but with a better patient acceptability and compliance compared with conventional PEG-4L. This new bowel preparation is an effective alternative as a low volume bowel preparation for screening colonoscopy which may improve the patient attitude to this procedure.

The invention claimed is:

1. A dry composition for reconstitution in 500 ml of aqueous solution, said composition comprising:
    (a) polyethylene glycol (PEG 4000): 52.500 g,
    (b) anhydrous citric acid: 0.813 g,
    (c) anhydrous sodium citrate: 1.863 g;
    (d) sodium chloride: 0.730 g;
    (e) potassium chloride: 0.370 g g/l;
    (f) anhydrous sodium sulphate: 3.750 g
    (g) simethicone 0.080 g
    (h) lime flavor 0.080 g, and
    (i) acesulfame potassium 0.130 g.

2. A product comprising the dry composition according to claim 1 and a laxative selected from bisacodyl, senna or sodium picosulphate.

3. A method for colon cleansing prior to prior to diagnostic, surgical or therapeutic procedures in the bowel, comprising the oral administration to a subject in need thereof of the reconstituted formulations of claim 1 in an amount sufficient to promote removal of solid residues and the cleansing of intestinal walls.

* * * * *